(12) United States Patent
Murray et al.

(10) Patent No.: US 10,265,158 B2
(45) Date of Patent: Apr. 23, 2019

(54) LIGAMENT ASSEMBLY

(71) Applicants: Biomet UK Healthcare Limited, Bridgend (GB); David Wycliffe Murray, Oxford (GB); Christopher Dodd, Oxford (GB); John Joseph O'Connor, Oxford (GB)

(72) Inventors: David Wycliffe Murray, Oxford (GB); Christopher Dodd, Oxford (GB); John O'Connor, Oxfordshire (GB); Russell Lloyd, Swindon Wiltshire (GB); Mohammed Imran Kahn, Berkshire (GB)

(73) Assignee: Biomet UK Healthcare Limited, Bridgend, South Wales (GB)

( * ) Notice: Subject to any disclaimer, the term of this patent is extended or adjusted under 35 U.S.C. 154(b) by 136 days.

(21) Appl. No.: 14/911,860

(22) PCT Filed: Jul. 31, 2014

(86) PCT No.: PCT/GB2014/052348
§ 371 (c)(1),
(2) Date: Feb. 12, 2016

(87) PCT Pub. No.: WO2015/022491
PCT Pub. Date: Feb. 19, 2015

(65) Prior Publication Data
US 2016/0193033 A1  Jul. 7, 2016

(30) Foreign Application Priority Data
Aug. 12, 2013 (GB) .................................. 1314408.4

(51) Int. Cl.
A61F 2/08   (2006.01)
A61F 2/38   (2006.01)

(52) U.S. Cl.
CPC .............. *A61F 2/0811* (2013.01); *A61F 2/08* (2013.01); *A61F 2/3886* (2013.01);
(Continued)

(58) Field of Classification Search
CPC .......................... A61F 2/08; A61F 2002/0852
See application file for complete search history.

(56) References Cited

U.S. PATENT DOCUMENTS 4,744,793 A * 5/1988 Parr ...................... A61F 2/0811
                                                      623/13.14
5,002,574 A * 3/1991 May ..................... A61F 2/0811
                                                      623/13.13
(Continued)

FOREIGN PATENT DOCUMENTS

BE        1010569 A6   10/1998
GB        2454251 A    5/2009
(Continued)

OTHER PUBLICATIONS

J. Dangel, Biomechanics of the anterior cruciate ligament and implications for surgical reconstruction, Strategies Trauma Limb Reconstruction. Apr. 2007.*
(Continued)

*Primary Examiner* — Yashita Sharma
(74) *Attorney, Agent, or Firm* — Schwegman Lundberg & Woessner, P.A.

(57) ABSTRACT

A ligament assembly comprising a first ligament anchor (9) connected to a second ligament anchor (14) by a ligament (18) a resilient element (40) being associated with the first ligament anchor (9) and a ligament tension adjuster (44, 50) being associated with the second ligament anchor (14). The resilient element (40) may be disposed within the first ligament anchor (9) and the ligament tension adjuster (44, 50) may be disposed within the second ligament anchor (14).

23 Claims, 4 Drawing Sheets

(52) U.S. Cl.
CPC . *A61F 2002/087* (2013.01); *A61F 2002/0835* (2013.01); *A61F 2002/0852* (2013.01); *A61F 2002/0864* (2013.01); *A61F 2002/0882* (2013.01); *A61F 2250/0012* (2013.01)

(56) References Cited

U.S. PATENT DOCUMENTS

| | | | |
|---|---|---|---|
| 5,004,474 A | | 4/1991 | Fronk et al. |
| 5,067,962 A | | 11/1991 | Campbell et al. |
| 5,507,812 A | * | 4/1996 | Moore ................... A61F 2/08 623/13.13 |
| 5,575,819 A | * | 11/1996 | Amis ................... A61F 2/08 623/13.13 |
| 2007/0049944 A1 | | 3/2007 | Stone |
| 2008/0288070 A1 | | 11/2008 | Lo |

FOREIGN PATENT DOCUMENTS

| | | | | |
|---|---|---|---|---|
| GB | 2517153 A | | 2/2015 | |
| WO | WO 97/36557 | * | 10/1997 | ............... A61F 2/08 |
| WO | WO-9736557 A1 | | 10/1997 | |
| WO | WO-9822048 A1 | | 5/1998 | |
| WO | WO-0245765 A2 | | 6/2002 | |
| WO | WO-2010017288 A1 | | 2/2010 | |
| WO | WO-2015022491 A1 | | 2/2015 | |

OTHER PUBLICATIONS

Mechanical properties of the scapholunate ligament correlate with bone mineral density measurements of the hand. Johnston. J Orthop Res Jul. 2004;22(4):867-71.*

"International Application Serial No. PCT/GB2014/052348, International Preliminary Report on Patentability dated Feb. 25, 2016", 11 pgs.

"International Application Serial No. PCT/GB2014/052348, International Search Report dated Jan. 22, 2015", 7 pgs.

"International Application Serial No. PCT/GB2014/052348, Written Opinion dated Jan. 22, 2015", 9 pgs.

"European Application Serial No. 14752912.7, Response filed Oct. 14, 2016 to Communication pursuant to Rules 161(1) and 162 EPC dated Apr. 4, 2016", 10 pgs.

"European Application Seriai No. 14752912.7, Office Action dated Jul. 31, 2017", 5 pgs.

"European Application Serial No. 14752912.7, Response filed Dec. 6, 2017 to Office Action dated Jul. 31, 2017", 12 pgs.

* cited by examiner

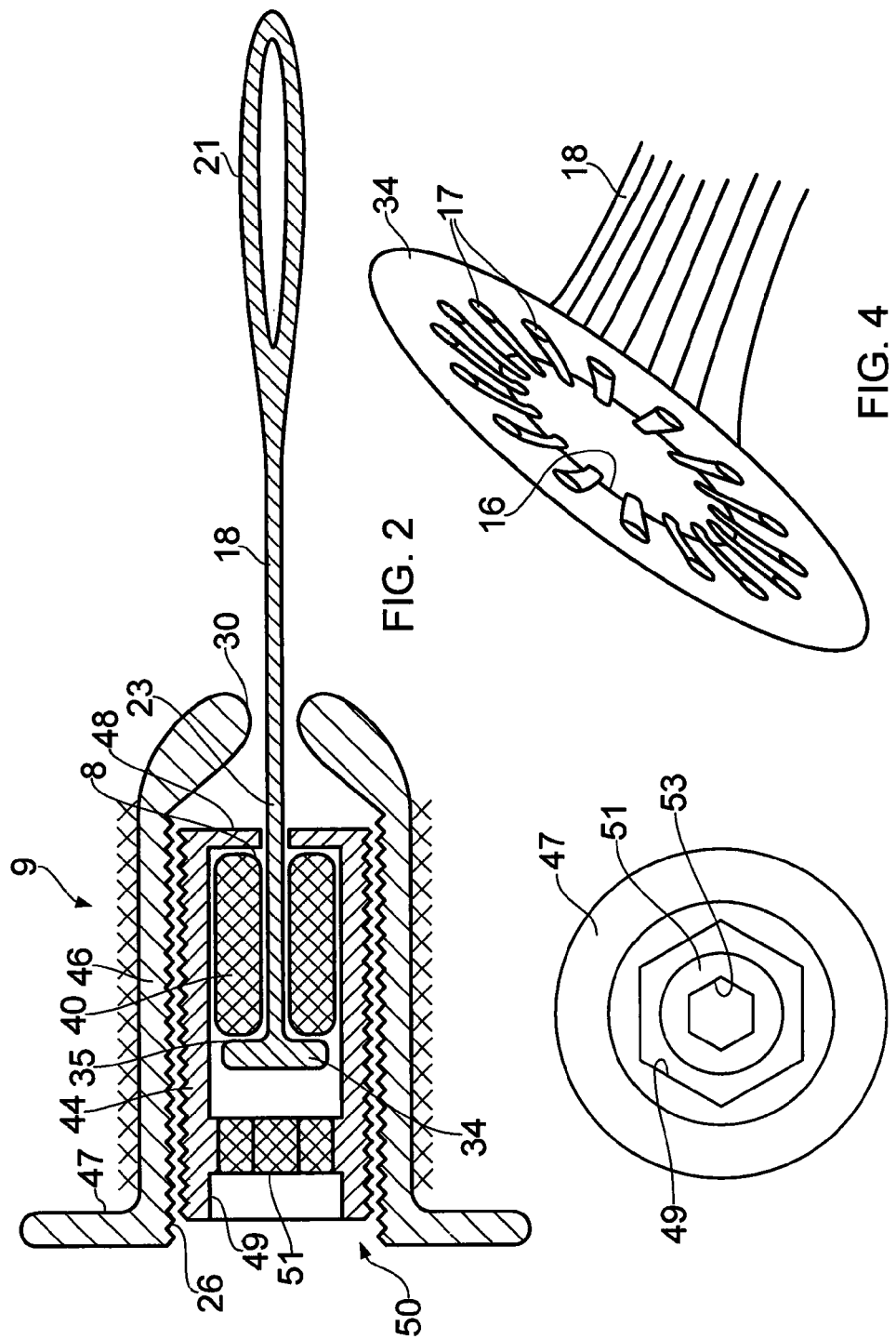

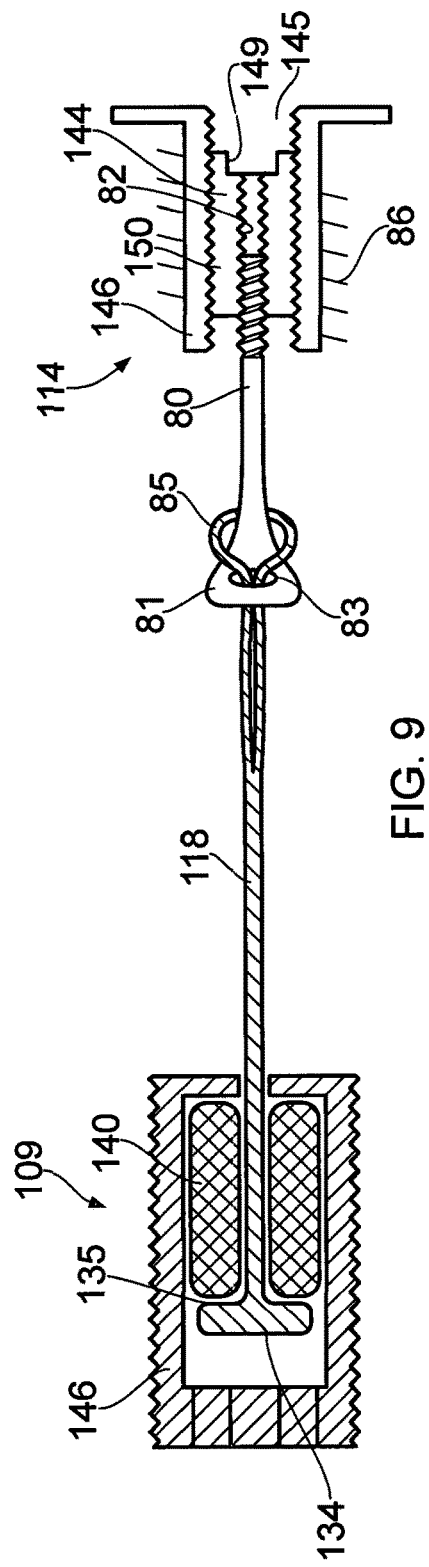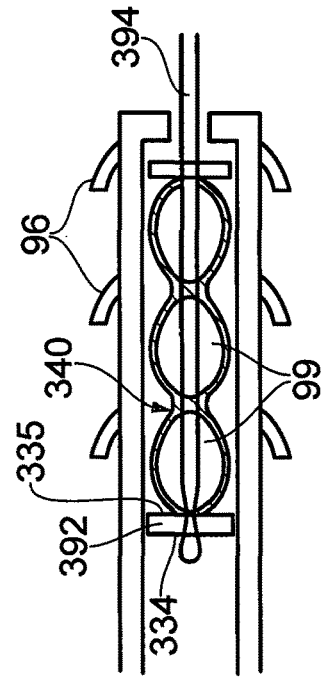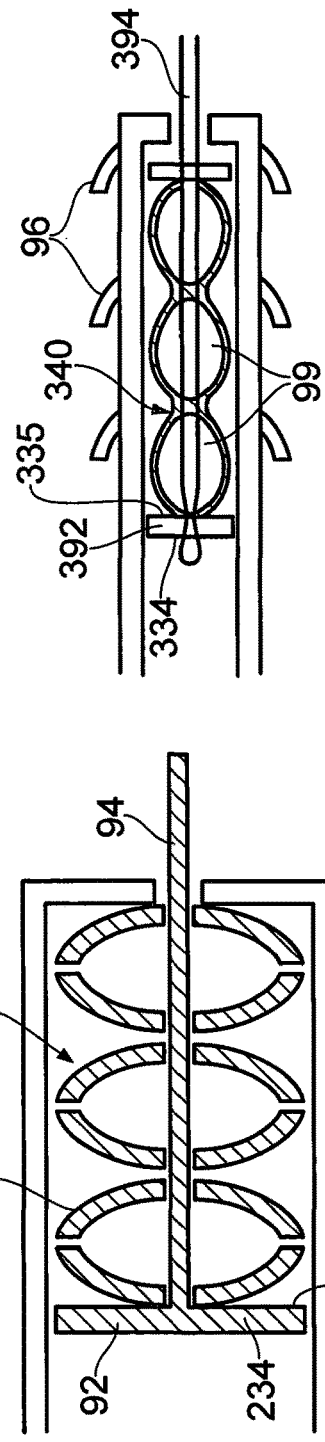
FIG. 9
FIG. 11
FIG. 10

LIGAMENT ASSEMBLY

CLAIM OF PRIORITY

This application is a U.S. National Stage Filing under 35 U.S.C. 371 from International Application No. PCT/GB2014/052348, filed on 31 Jul. 2014, published as WO 2015/022491 A1, which claims the benefit of United Kingdom Application No. 1314408.4 filed on 12 Aug. 2013, the benefit of priority of each of which is claimed hereby, and each of which are incorporated by reference herein in its entirety.

This invention relates to improvements in ligament assemblies and particularly, although not exclusively, relates to improving the connection between a ligament and a ligament anchor.

BACKGROUND

It is known to implant an artificial/prosthetic ligament to replace a natural ligament which has become damaged. Conventional artificial ligaments are formed from strands or bundles of artificial fibres which may be woven and/or aligned to form a flexible member which is substantially uniform in size and is resilient along its length.

A natural ligament exhibits high strength, toughness and resilience and retains these properties for many years. To date, it has been impossible to match these properties using artificial fibres.

When implanted, artificial ligaments can be attached to existing bone tissue as long as the attachment site is relatively intact. However, if surrounding bone tissue is significantly diseased or damaged, it may be necessary to remove both the natural ligament and the adjacent bone tissue and replace them with prosthetic components. In severe cases of disease or damage, the natural joint may be replaced with a total joint replacement prosthesis.

When implanting a total joint replacement prosthesis, both cruciate ligaments are often lost. The functionality of the ligaments must then be replicated as closely as possible by one or more features of the replacement prosthesis (as for example in the case of a cooperating cam and post in a total knee replacement). However, it has proved extremely difficult to replicate the natural kinematics of a joint without the presence of naturally functioning ligaments. This is particularly evident in the case of the knee joint, which exhibits a complex movement that is highly dependent upon the interaction of ligaments with the articulating areas of bone.

Joint replacement prostheses commonly comprise two bone engaging components that articulate via a bearing component. In a total knee replacement prosthesis, the bone engaging components are a femoral component, comprising an anterior surface with patella track and two femoral condyles, and a tibial component, comprising a substantially planar surface or tray and a post, keel or other stabilising feature. The femoral and tibial components articulate via a bearing component mounted on the tray of the tibial component. The bearing component may be fully or partially fixed with respect to the tibial component, and commonly comprises a single piece of high density polyethylene.

In order to more closely replicate the natural kinematics of the knee, it is desirable for a total knee replacement prosthesis to facilitate a combination of rolling, rotational and translational movement between the femoral and tibial components of the prosthesis. This can be achieved in part by employing a "mobile" bearing component, having some freedom of movement relative to the tibial component on which it is supported. In addition, it has been shown that mobile bearing components exhibit more favourable wear characteristics than so called "fixed" meniscal bearings.

When the wear in the knee joint is limited to only one medial or lateral compartment, it is known to replace only the bearing surface of the femoral condyle and the cooperating portion of the tibia of that compartment with a partial or "uni-compartmental" joint replacement prosthesis. Particularly where such a prosthesis uses a mobile bearing, there will be an increased risk of dislocation in the event of joint distraction, if one or more of the ligaments of the knee are diseased or otherwise damaged. With this in mind, it would be very advantageous to be able to implant an artificial/prosthetic ligament during the joint replacement procedure to restore full stability and maintain natural joint articulation.

STATEMENTS OF INVENTION

According to the present invention there is provided a ligament assembly comprising a first ligament anchor connected to a second ligament anchor by a ligament, a resilient element being associated with the first ligament anchor and a ligament tension adjuster being associated with the second ligament anchor.

The resilient element may be disposed between the artificial ligament and the first ligament anchor and the ligament tension adjuster may be disposed between the artificial ligament and the second ligament anchor.

The resilient element may be housed within the first ligament anchor and/or the ligament tension adjuster may be housed within the second ligament anchor.

The resilient element may form part of the first ligament anchor and/or the ligament tension adjuster may form part of the second ligament anchor.

According to another aspect of the present invention, there is provided a ligament assembly comprising a ligament having an attachment shoulder with an annular face.

According to another aspect of the present invention, there is provided a ligament assembly comprising a ligament having an attachment shoulder which is a separate component from the ligament.

The attachment shoulder may have an annular face. The annular face may be continuous and/or may be substantially planar.

The use of the attachment shoulder ensures that the ligament anchor does not squeeze, clamp, or otherwise abrade the ligament.

The ligament assembly may further comprise a ligament anchor, the annular face of the shoulder directly or indirectly engaging the ligament anchor.

The ligament assembly may further comprise a resilient element and/or a ligament tension adjuster. The annular face of the shoulder may engage the resilient element and/or the ligament tension adjuster directly or indirectly.

The shoulder may be integrally formed with the ligament. The shoulder may be moulded with the ligament or moulded onto the ligament. Alternatively, the shoulder may comprises a separate or discrete member attached to the artificial ligament. The discrete member may comprise a plurality of fixing structures for connection to the artificial ligament. The shoulder may comprise a washer.

The shoulder may comprise a washer.

The ligament may be a natural ligament, a ligament grown in vitro, or a prosthetic/artificial ligament.

A thread may affix the shoulder to the ligament. The shoulder comprise a plurality of holes to receive the thread.

The thread and the artificial ligament may be unitary. The thread may be knotted, tied, glued or otherwise fixed to the ligament.

The ligament anchor may comprise a porous surface for osteointegration.

The ligament anchor may comprise a threaded surface to allow engagement with a bone of a patient.

The artificial ligament may be fully rotatable relative to the ligament anchor.

A distal portion of the artificial ligament may comprise a loop. The loop may be sized to slip over a bollard of the ligament anchor.

At least a distal portion of the artificial ligament may comprise a plurality of strands and/or fibres that extend through a hole in a bollard of the ligament anchor and connect back to the artificial ligament.

The shoulder may comprise a disc with perforations. The strands or fibres of the artificial ligament may be passed through the perforations.

The ligament assembly may further comprise a resilient element disposed between the artificial ligament and the ligament anchor, the resilient element modifying the effective stiffness of the artificial ligament.

The resilient element may have a stiffness approximating that of a natural ligament that is to be replaced. In this manner, the resilient element may assist in replicating the natural characteristics of the joint. The resilient element may have linear or non-linear stiffness characteristics which may be achieved by methods known in the art. The stiffness of the resilient element may be in a range of 3 N/mm to 40 N/mm.

The resilient element may comprise one or more springs and/or one or more elastic or elastomeric members and/or one or more Belleville washers. The resilient element may comprise a cylinder, tube, toroid, cone or loop of elastic or elastomeric material. If the resilient element is conical, it can provides variable stiffness over its range of movement.

The resilient element may encircle the artificial ligament.

The resilient element may engage an abutment at a predetermined position in its range of movement to vary the effective stiffness of the resilient element.

The shoulder may be provided at or near one end of the ligament. The resilient element may engage the shoulder via a bearing component.

The resilient element may have a linear stiffness characteristic. Alternatively, the resilient element may have a non-linear stiffness characteristic.

The ligament tension adjuster may be operable to adjust the tension within the ligament. The ligament tension adjuster therefore enables the tension in the ligament to be adjusted in a controlled manner, independently and controllably altering the characteristics of the ligament.

The ligament tension adjuster may comprise a carrier element. The carrier element may act between the ligament anchor and the artificial ligament.

The tension may be adjusted by adjusting the position of the carrier element relative to a body of the second ligament anchor. Thus tension in the ligament may be altered even after both the ligament and the first and second ligament anchors have been implanted into a patient. For example, the carrier element may retain an end of the ligament and may be translated along the second ligament anchor to adjust the position of the end of the ligament relative to the first ligament anchor.

The adjustment means may comprise a threaded connection between the carrier element and the body of the second ligament anchor. The carrier element may have an external thread and the second ligament anchor may have a corresponding internally threaded bore within which the carrier element is received. The tensioning element may be configured to be screwed into or out of the bore to adjust the tension in the ligament.

The tensioning element may be accessed through an opening formed in the ligament anchor.

The ligament assembly may comprise at least part of a knee replacement prosthesis in which the ligament anchor comprises a tibial component and the ligament comprises a replacement anterior cruciate ligament (ACL).

An advantage of this invention is improved kinematics. Artificial ligaments without suitable stiffness characteristics do not balance with the other soft tissue, resulting in abnormal kinematics. By using a ligament with physiological stiffness, there will be mutual respect with the retained soft tissue, allowing the joint to function normally.

Another advantage of the resilient element and/or tensioning element is that they protect the ligament from excess load. It has been shown that the loads induced in an artificial ligament which is substantially inextensible are far in excess of the ultimate tensile stress of a natural ligament. By allowing just a small amount of extension in the artificial ligament, these loads are reduced and the ligament and its attachment are protected.

A further advantage of the resilient element and/or tensioning element is that they enable the tension of the ligament to be balanced with other soft tissues. This eases the implantation of an artificial ligament because fixation can be optimised first before applying tension to a ligament. In embodiments with an adjustable tensioning element and/or with adjustable fixation of the ligament to the femur, a single size or limited range of sizes of artificial ligament can be used on any patient. This reduces the inventory requirements for artificial ligaments.

According to another aspect of the present invention, there is provided a method of implanting into a bone an artificial ligament having a shoulder formed on a first end, the method comprising: (a) forming a bore through the bone; (b) inserting a second end of the artificial ligament through the bore; (c) drawing the artificial ligament through the bore until a substantially planar annular face of the shoulder abuts the bone.

The method may further comprise connecting the second end of the artificial ligament to a ligament anchor.

The method may further comprise adjusting the position of an adjustable tensioning element until a predetermined tension within the artificial ligament is achieved.

According to another aspect of the present invention there is provided a ligament assembly comprising a ligament and a ligament anchor, the ligament anchor comprising a bollard having a bore adapted to receive all or part of the ligament or a thread or cord for attaching the ligament to the bollard.

The ligament, part ligament, thread or cord may extend through the bore and be tied off to prevent it passing back through the bore. The ligament, part ligament, thread or cord may be wound around the anchor and pass back over itself, so that tension in the ligament, part ligament, thread or cord causes the ligament, part ligament, thread or cord to grip itself more tightly, and thereby to increase the tear out force required to pull the ligament away from the ligament anchor.

Additionally or alternatively, the ligament, part ligament, thread or cord may be further affixed (e.g., with adhesive). The cord or thread may be unitary with the ligament (e.g., the cord or thread may form with the ligament a single, homogenous length of material.

The term artificial ligament may include, but is not limited to, a fibre or strands (e.g., bundles) of (e.g., artificial) fibres which may be woven, braided, and/or aligned. E.g., the artificial ligament may be a flexible member which is substantially uniform in size and/or is resilient along its length. The artificial ligament may not be resilient along its length, e.g., it may not stretch significantly under load. For example, the artificial ligament may not stretch more than 0.5 millimeters, under a load when installed in a human patient. An artificial ligament may be used other than as a replacement for a natural ligament as existed or exists in the human or animal body.

The artificial ligament may comprise any suitable material or combinations of materials. The material may be a biocompatible material such as polyester fibre(s) or ultra-high-molecular-weight polyethylene fibre(s). The ligament may be formed from ultra high molecular weight polyethylene fibre braid, such as the product sold as Dynema.

The ligament anchor(s) may also be made of any suitable material or combinations of materials. The material may be a biocompatible material such as plastics material, stainless steel or titanium.

BRIEF DESCRIPTION OF THE DRAWINGS

For a better understanding of the present invention, and to show more clearly how it may be carried into effect, reference will now be made, by way of example, to the accompanying drawings, in which:

FIG. 2 is a cross-sectional schematic view of a first ligament anchor for use in the ligament assembly of FIG. 1;

FIG. 3 is a view on arrow A in FIG. 2, and is an end view of the first ligament anchor;

FIG. 4 is a perspective view of one possible construction of ligament attachment shoulder for connection to the first ligament anchor of FIG. 2;

FIG. 9 is a schematic view of an alternative form of ligament assemble with a resilient element in a first ligament anchor and a tension adjusting device in a second ligament anchor;

FIG. 10 is a schematic view of a first ligament anchor using spring/Belleville washers as the resilient element;

FIG. 11 is a schematic view of a first ligament anchor using multiple elastomeric members as the resilient element.

DETAILED DESCRIPTION

Figure 1:
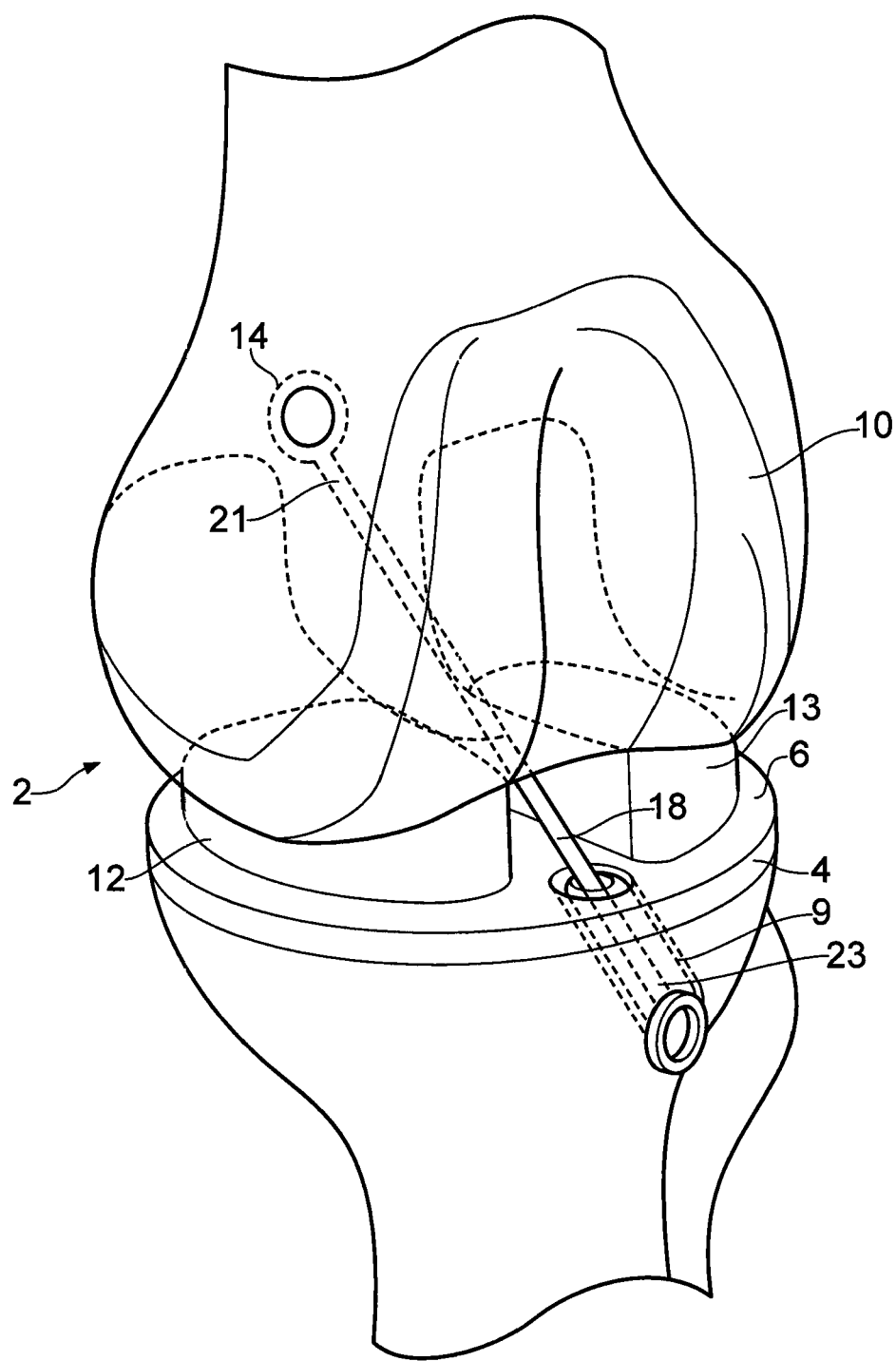
FIG. 1 is a schematic view of a ligament assembly implanted in a knee.

FIG. 1, illustrates a knee joint in which is implanted a total joint replacement prosthesis and a ligament assembly. However, it will be appreciated that the ligament assembly described herein can be used with a partial joint replacement prosthesis, or on a knee joint without any form of joint replacement prosthesis.

Referring to FIG. 1, a knee joint is fitted with a prosthesis 2 comprising a tibial component 4 having a tibial tray 6 integrally formed with a stem (not shown), a femoral component 10 and a pair of bearing components 12, 13. The bearing components 12, 13 separate the tibial component 4 and femoral component 10, and are formed with proximal and distal bearing surfaces which engage corresponding bearing surfaces on the tibial tray 6 and on the femoral component 10. These various bearing surfaces enable the tibial component 4 to rotate and translate relative to the femoral component 10. The bearing components 12, 13 may, for example, be meniscal bearing components, rotational platform bearing components, fixed bearing components or joined bearing components An artificial ligament 18 is connected at one end 21 to the femoral component 10, or to the femur by means of a second ligament anchor 14. Any means of connection of the end 21 of the ligament 18 to the ligament anchor 14 is contemplated. For example, the ligament anchor 14 may comprise a boss or peg formed on the femoral component for attachment of the ligament 18, or the ligament anchor 14 may comprise a bone anchor screwed cemented or otherwise fixed to the femur. The end 21 of the ligament 18 may be folded over and glued, sewn or otherwise fixed to form a loop (not shown). Alternatively, a hole or eye may be formed in the end 21 of the ligament 18. The ligament 18 may then be secured to the ligament anchor 14 by passing the loop or eye over the boss. The boss may have an enlarged head and narrower stem to encourage stable fixation of the ligament 18 once attached to the boss.

With reference also to FIG. 2, the other end 23 of the artificial ligament 18 is attached to a resilient element 40 supported within a carrier element 44 of a first ligament anchor 9. Any convenient means of connection between the end 23 of the ligament 18 and the carrier element 44 is contemplated. In the illustrated embodiment, the end 23 of the ligament 18 passes through a passage 8 which may be moulded or otherwise formed in the resilient element 40 and is prevented from being pulled out of the resilient element 40 by a shoulder 34 having a substantially planar annular face 35 which is of larger diameter than the bore 8. The shoulder 34 may be integrally formed with the ligament 18, or may for example, comprise a discreet component such as a disc or washer which is threaded onto the ligament 18.

FIG. 4 illustrates one possible arrangement of discreet shoulder 34 in the form of a washer having a central bore 16 and a plurality of openings 17 distributed around its circumference. In this arrangement, the ligament 18 is multi-stranded and separates into individual strands or bundles of strands as it passes through the central opening 16. The strands or bundles of strands each then pass back through a respective opening 17 and may be tied off glued or otherwise fixed to prevent them being pulled back through the openings 17.

The resilient element 40 may take many forms, such as one or more coil springs, one or more polymeric or elastomeric elements or Bellville washers, but in the illustrated embodiment comprises a cylinder of elastomeric material. An appropriate carrier element 44 is selected in order to properly house and support the chosen resilient element 40.

As illustrated in FIG. 2, the first ligament anchor 9 comprised an outer sleeve 46 terminating in a bone engaging flange 47 at one end and in a ligament guiding mouth 30 at the opposite end. The resilient element 40, and carrier element 44 are received within a cylindrical bore 26 formed in the outer sleeve 46 of the ligament anchor 9. The ligament 18 extends through the passage 8 formed in the resilient element 40, through an aligned opening in an end plate 48 of the carrier element 44 and emerges from the mouth 30 of the sleeve 46. The mouth 30 is rounded and polished to minimize wear of the ligament.

The shoulder 34 prevents the ligament 18 passing through the passage 8, and spreads the load from the ligament 18 over a first end of the resilient element 40, so that when tensile forces are applied to the ligament 18, the shoulder 34 bears against the first end of the resilient element 40, forcing the opposite end of the resilient element against the end plate 48, thereby compressing the resilient element 40.

The resilient element 40 assists in replicating the natural stiffness of the ligament that is to be replaced by the ligament 18. The characteristics of the resilient element 40 are therefore selected to be similar to those of the natural ACL.

The carrier element 44 has a cylindrical outer surface which is threaded and engages a corresponding internal thread formed in the outer sleeve 46 of the ligament anchor 9.

The end of the carrier element 44 opposite to the end plate 48 is provided with a first tool drive formation 49 closed off by an end plug 51 in the form of a grub screw. As best shown in FIG. 3, the tool drive formation 49 comprises a hex drive recess which can be engaged by an appropriately sized hex drive key, but any other form of tool drive such as a slot or posi-drive recess are contemplated.

Similarly, the end plug 51 is provided with a second tool drive formation 53 such as a another hex drive recess which can be accessed through the first tool drive formation 49. The end plug 51 can be unscrewed from the carrier element 44 by an appropriately sized hex drive key. With the end plug 51 unscrewed from the carrier element 44, the interior of the carrier element 44 can be accessed during assembly.

The externally threaded carrier element 44 holds an end of the ligament 18 and can be screwed into and out of the threaded outer sleeve 46. It can therefore be used as a ligament tensioning element 50, the operation of which is described below.

Method of Assembly of Ligament Anchor

Pre-operatively, the ligament 18 and resilient element 40 are assembled into the carrier element 44, with the end plug 51 removed, such that the ligament 18 extends through the passage 8 formed in the resilient element 40 and through the aligned opening in an end plate 48 of the carrier element 44. The carrier element 44 is then screwed to its initial position in the outer sleeve 46 of the ligament anchor 9, such that the ligament 18 extends through the mouth 30 of the bore 26 formed in the outer sleeve 46. As mentioned above, the shoulder 34 prevents the ligament 18 passing through the passage 8 so the ligament 18 is captive in the ligament anchor 9 when the end plug 51 is screwed back into the carrier element 44.

Method of Implanting Ligament Assembly

In one possible procedure, a hole 45 is drilled through the tibia with a surgical drill for receiving the first ligament anchor 9. Then, using standard surgical technique, the femoral component 10 is implanted into a distal end of a femur (not shown) and the tibial component 4 is implanted into a proximal end of a tibia (not shown), such that the stem 8 is located in the intramedulary canal of the tibia, and the tiblal tray 6 rests on the resected proximal end of the tibia. The appropriate bearing component(s) are placed between the femoral component 10 and the tibial component 4.

The end 21 of the ligament 18 is then threaded through the hole 45 in the tibia, and the outer sleeve 46 of the ligament anchor 9 is cemented, screwed or otherwise secured in the hole 45, such that the flange 47 seats against the outer surface of the tibia or, where the bore is countersunk, against the countersunk surface formed in the tibia.

The end 21 of the ligament 18 is then attached to the femoral component 10 by passing the loop or eye over the ligament anchor 14.

The joint is then examined to determine whether the tension in the ligament 18 is balanced with the tension in the retained posterior cruciate ligament (PCL). If the tension in the artificial ligament 18 is balanced with that in the PCL, the implantation procedure is complete. If the tension in the artificial ligament 18 is not balanced with that in the PCL, the position of the carrier element 44 within the bore 26 is adjusted, so as to increase or reduce the tension applied to the ligament 18. A tool (not shown) is inserted into the tool drive formation 49. By rotating the tool, the carrier element 44 is rotated and moves axially along the internal thread in the bore 26, thereby adjusting the tension in the artificial ligament 18.

Figure 5:
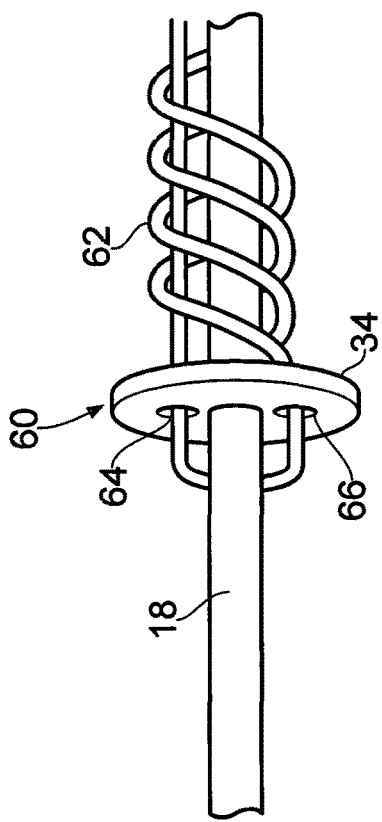
FIG. 5 is a perspective view of another possible construction of ligament attachment shoulder for connection to the first ligament anchor of FIG. 2.

FIG. 5 shows an alternative form of ligament fixing in which the shoulder 34 is defined by a perforated washer 60 which fits over the ligament 18 and is tied to the ligament 18 by a thread 62. The thread 62 passes along the ligament 18, through a first opening 64 in the perforated washer 60, is threaded back through a second opening 66 in the washer and is then wound around the ligament 18 in the manner of a fly fishing knot. As the ligament 18 is pulled away from the ligament anchor, the thread 62 tightens on itself and on the ligament 18, thereby increasing the fixation of the washer 60 the ligament 18.

Figure 6:
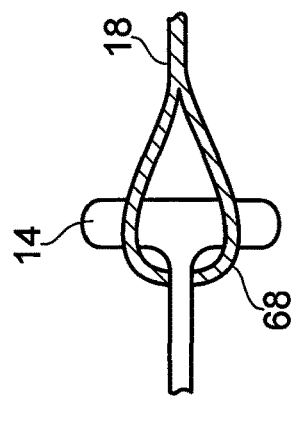
FIG. 6 is a perspective view of a possible construction of ligament attachment for connection to a second ligament anchor.

FIG. 6 shows a modified "bollard" type ligament anchor 14 which is substantially T-shaped. A loop 68 formed in the end of the ligament 18 is slipped over the T-shaped ligament anchor 14 and fixes the ligament 18 to the ligament anchor 14.

Figure 7:
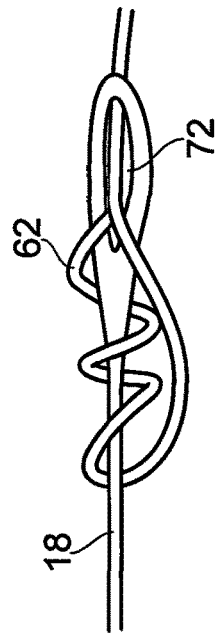
FIG. 7 is a perspective view of another possible construction of ligament attachment for connection to a second ligament anchor.

FIG. 7 shows a modified "bollard" type ligament anchor 14 having an opening 70 through which all or part of the width of the ligament 18 is passed. After passing through the opening, the ligament or the part of the ligament is wound back on itself and is tied off, glued or otherwise secured to the ligament anchor. In the illustrated embodiment, the ligament 18 is split into two separate portions at its distal end. To attach this ligament 18 to ligament anchor 14, the ends of the ligament 18 are extended after passing through the opening 70 and are wrapped around opposite sides of the ligament anchor 14, where they can be tied together, glued or otherwise secured.

Figure 8:
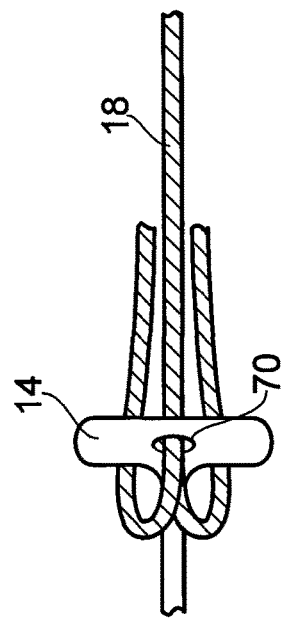
FIG. 8 is a perspective view of another possible construction of ligament attachment for connection to a second ligament anchor.

FIG. 8 is a perspective view of a ligament 18 tied to a ligament anchor (not shown) by a thread 62. The thread 62 is formed into a loop which is then wound around the ligament 18 in the manner of a fly fishing knot and threaded back through an eye 72 formed in the ligament. As the ligament 18 is pulled away from the ligament anchor, the thread 62 tightens on itself and on the ligament 18, thereby increasing the fixation of the thread 62 to the ligament 18.

FIG. 9 shows a ligament assembly in which the resilient element 140 is provided in a first ligament anchor 109 and a ligament tensioning device 150 is provided on the opposite end of the ligament 118 in a second ligament anchor 114. In the embodiment of FIG. 2, both the resilient element 40 and the tensioning device 50 are provided in a single ligament anchor 9. Where space for implanting the ligament anchor is not limited, the dual function ligament anchor 9 of FIG. 2 is particularly efficient and cost effective. However, where space for implanting the ligament anchor is limited, the single function ligament anchors 109, 114 of FIG. 9 are beneficial because they can be made smaller than the combined function ligament anchor 9 of FIG. 2. More specifically, the resilient element 140 can be fitted directly into the sleeve 146 of the first ligament anchor 109, and the sleeve 146 can be of smaller diameter because it does not need to accommodate the carrier element 144. Furthermore, the space for providing a tool receiving recess is not required, so the sleeve 146 can be made shorter, or the length of the resilient element 140 (and the ligament 118) can be made longer. This may be helpful in achieving the desired tension characteristics from a resilient element 140 (and cooperating ligament shoulder 134) of smaller diameter.

The ligament 118 extends between the ligament anchors 109 and 114 and is connected to the first ligament anchor 109 by means of a shoulder 134, in the same manner as described above in relation to the embodiment of FIG. 2.

The second ligament anchor 114 may comprise a perforated or imperforate "bollard" type ligament anchor. In the embodiment illustrated in FIG. 9, the second ligament anchor 14 comprises a threaded shaft 80 with a tapered polished head 81 having a centrally disposed opening 83. The shaping and polishing of the head 81 increases the contact area and reduces the stress in the ligament 118 where it contacts the head and reduces the possibility of damage to the ligament such as from fretting in service. In addition, the opening 83 is chamfered and polished to achieve a smooth fenestration which further increase the contact area and lowers the stress in the ligament.

A loop 85 formed at the end of the ligament 118 passes through the opening 83 and is extended to reduce the local stresses in the ligament 118 where it is split to form the loop 85.

The externally threaded shaft 80 is received within a threaded bore 82 in a carrier element 144 of the second ligament anchor 114. The carrier element 144 is screwed into an outer sleeve 146 which is adapted to be screwed, cemented or otherwise fixed into bone. For example, the carrier element may have an external coarse thread 86 for cutting into bone.

The cooperating threads between the shaft 80 and bore 82 are oppositely handed relative to the cooperating threads between the carrier element 144 and the outer sleeve 146. Therefore as one set of threads is left handed and the other set of threads is right handed, the tension adjuster 150 acts as a turnbuckle.

A tool drive formation 149, which may for example comprise a hex drive recess, is provided in an and of the carrier element 144, which can be accessed through an open end 145 of the outer sleeve 146. A suitable tool (such as a hex drive key) may be used to engage in the tool drive formation and screw the carrier element 144 in or out of the sleeve 146 to adjust the tension in the ligament 118 intraoperatively, as in the embodiment of FIG. 1. It will be appreciated that as oppositely handed threads are used and the threaded rod 80 of the ligament anchor 114 must be prevented from turning to prevent it twisting the ligament 118, as the carrier element is turned in a first direction the threaded rod 80 will be drawn into the carrier element 144 and the carrier element will be drawn towards the end 145 of the outer sleeve 146. Thus the tension in the ligament 118 will be increased. Whereas, as the carrier element 144 is turned in the opposite direction, the relative translation will be in the opposite direction and the tension in the ligament 118 will be reduced.

In an alternative embodiment, not illustrated, the carrier element 144 may be held axially captive in the outer sleeve 146, for example by circlips, but may be free to rotate relative to the outer sleeve 146. Thus as the carrier element 144 is rotated in a first direction the threaded rod 80 will be drawn in to the carrier element 144 and the tension in the ligament will be increased. Whereas, as the carrier element 144 is turned in the opposite direction, the relative translation will be in the opposite direction and the tension in the ligament 118 will be reduced.

FIG. 10 is a schematic cross-sectional view of a resilient member 240 comprising a plurality of conical spring washers 90 stacked along their central axis. Opposing washers have opposite curvatures, as depicted, but other arrangements are contemplated. Fewer or more washers 90 may be included, e.g., to provide a desired level of resiliency and/or displacement (e.g., position) under load from the ligament. In this embodiment the shoulder 234 comprised a washer 92 fixed to a shaft 94, which is attached to the ligament by a bollard (not illustrated). An annular face 235 of the shoulder 234 bears directly on the end spring washer and transfers load from the ligament into the spring washers 90.

FIG. 11 is a schematic cross-sectional view of a segmented resilient member 340. The segmented resilient member may be formed from a single resilient component shaped to include a plurality of constricted portions along its length or may be made up from a plurality of discreet resilient components 99 supported on a central shaft 394.

In this embodiment the shoulder 334 comprised a washer 392 fixed to the shaft 394. An annular face 335 of the shoulder 334 bears directly on the end resilient component 99 and transfers load from the ligament into the resilient components 99.

One or more substantially radial protrusions 96 are fixed to an outside surface of the outer sleeve 346 to provide bone anchorage instead of or in addition to threads formed on the outer sleeve 346. The radially extending protrusions 28 may extend in any direction from the body, e.g., circumferentially around the outer surface and/or angled towards or away from the distal end of the artificial ligament, as necessary to achieve adequate fixation.

Although in the illustrated embodiment the ligament assembly is used with a total knee joint replacement prosthesis, one or both of the first and second ligament anchors 9, 14 can be implanted directly into bone, or one or both may be fixed to respective prosthetic components which are themselves attached to bone. As mentioned above, the ligament assembly may be used with a joint replacement prosthesis which replaces only part of a joint. For example it may be used with a partial knee replacement prosthesis which replaces only a single femoral condyle and a corresponding portion of the tibia.

When used with a total or partial knee prosthesis the ligament anchor, 9, 14 may be fixed to respective components of the prosthesis or may be fixed directly or indirectly onto or into a bone. Also, one or more parts of the prosthesis may be specifically shaped to accommodate the ligament during at least part of the range of articulation of the prosthesis. For example, a cut out, hole or ligament deflecting element, which changes the line of action of the ligament, may be provided in or on the prosthesis To avoid unnecessary duplication of effort and repetition of text in the specification, certain features are described in relation to only one or several aspects or embodiments of the invention. However, it is to be understood that, where it is technically possible, features described in relation to any aspect or embodiment of the invention may also be used with any other aspect or embodiment of the invention.

The invention claimed is:

1. A ligament assembly comprising: a first ligament anchor connected to a second ligament anchor by a ligament that comprises a shoulder with a substantially annular face, a resilient element being at least partially disposed within a body of the first ligament anchor, wherein the resilient element comprises a cylinder of elastomeric material that encircles the ligament, and a ligament tension adjuster being at least partially disposed within a body of the second ligament anchor, the ligament tension adjuster including a carrier element that retains an end of the ligament, the carrier element having an externally threaded surface that engages an internally threaded surface of the body of the second ligament anchor to allow translation of the carrier element along the body of the second ligament anchor.

2. The ligament assembly as claimed in claim 1, in which the resilient element is disposed between the artificial ligament and the first ligament anchor and the ligament tension adjuster is disposed between the artificial ligament and the second ligament anchor.

3. The ligament assembly as claimed in claim 1, in which the resilient element forms part of the first ligament anchor and the ligament tension adjuster forms part of the second ligament anchor.

4. The ligament assembly as claimed in claim 1, in which the annular face is continuous.

5. The ligament assembly as claimed in claim 4, in which the annular face is substantially planar.

6. The ligament assembly as claimed in claim 1, in which the shoulder is integrally formed with the ligament.

7. The ligament assembly as claimed in claim 1, in which the shoulder is provided with at least one hole.

8. The ligament assembly as claimed in claim 7, in which all or part of the ligament is threaded through the hole.

9. The ligament assembly as claimed in claim 1, in which the shoulder comprises a discrete element which is attached to the ligament.

10. The ligament assembly as claimed in claim 1, in which the annular face of the shoulder engages the resilient element directly.

11. The ligament assembly as claimed in claim 1, in which the ligament comprises a loop, adapted for attachment to the second ligament anchor.

12. The ligament assembly as claimed in claim 1, in which the ligament is an artificial ligament.

13. The ligament assembly as claimed in claim 1, in which the resilient element modifies the effective stiffness of the ligament.

14. The ligament assembly as claimed in claim 13, in which the stiffness of the resilient element is within the range of 3 to 40 N/mm.

15. The ligament assembly as claimed in claim 1, in which the resilient element comprises a cylinder, tube, toroid or cone of elastomeric material.

16. The ligament assembly as claimed in claim 1, in which the resilient element encircles the ligament.

17. The ligament assembly as claimed in claim 1 comprising at least part of a knee replacement prosthesis, in which the ligament comprises a replacement anterior cruciate ligament (ACL).

18. A ligament assembly comprising: a first ligament anchor connected to a second ligament anchor by a ligament that comprises a shoulder with a substantially annular face, a resilient element being at least partially disposed within a body of the first ligament anchor, wherein the resilient element comprises a cylinder of elastomeric material that encircles the ligament, and a ligament tension adjuster being at least partially disposed within a body of the second ligament anchor, the second ligament anchor comprising a bollard adjustably coupled to the ligament tension adjuster and having a bore adapted to receive the ligament or part of the ligament, the ligament tension adjuster including a carrier element having an externally threaded surface that engages an internally threaded surface of the body of the second ligament anchor to allow translation of the carrier element along the body of the second ligament anchor.

19. The ligament assembly as claimed in claim 18, in which the ligament or part ligament is configured to extend through the bore and be tied off or otherwise fixed to prevent it passing back through the bore.

20. The ligament assembly as claimed in claim 19, in which the ligament or part ligament is wound around the ligament anchor and passes back over itself.

21. The ligament assembly as claimed in claim 18, in which the annular face is continuous.

22. The ligament assembly as claimed in claim 21, in which the annular face is substantially planar.

23. The ligament assembly as claimed in claim 22, wherein the annular face of the shoulder engages the resilient element directly.

* * * * *